United States Patent
Demarais et al.

(10) Patent No.: US 6,945,977 B2
(45) Date of Patent: *Sep. 20, 2005

(54) SYSTEMS AND METHODS FOR CLOT DISRUPTION AND RETRIEVAL

(75) Inventors: Denise Demarais, Los Gatos, CA (US); Michael A. Evans, Palo Alto, CA (US); Stephen A. Leeflang, Stanford, CA (US); Christian S. Eversull, Palo Alto, CA (US)

(73) Assignee: Bacchus Vascular, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/680,367

(22) Filed: Oct. 6, 2003

(65) Prior Publication Data

US 2004/0082962 A1 Apr. 29, 2004

Related U.S. Application Data

(63) Continuation of application No. 10/162,276, filed on Jun. 3, 2002, now Pat. No. 6,660,014, which is a continuation of application No. 09/454,517, filed on Dec. 6, 1999, now Pat. No. 6,454,775.

(51) Int. Cl.$^7$ ............................................. A61B 17/22
(52) U.S. Cl. ...................................... 606/128; 606/159
(58) Field of Search ................................. 606/128, 159, 606/113, 114, 127, 115

(56) References Cited

U.S. PATENT DOCUMENTS

| | | |
|---|---|---|
| 3,320,957 A | 5/1967 | Sokolik |
| 4,621,636 A | 11/1986 | Fogarty |
| 4,646,736 A | 3/1987 | Auth |
| 4,665,906 A | 5/1987 | Jervis |
| 4,732,154 A | 3/1988 | Shiber |
| 4,762,130 A | 8/1988 | Fogarty et al. |
| 4,819,634 A | 4/1989 | Shiber |
| 4,842,579 A | 6/1989 | Shiber |
| 4,883,458 A | 11/1989 | Shiber |
| 4,886,490 A | 12/1989 | Shiber |
| 4,894,051 A | 1/1990 | Shiber |
| 4,895,166 A | 1/1990 | Farr et al. |
| 4,923,462 A | 5/1990 | Stevens |
| 4,926,858 A | 5/1990 | Gifford, III et al. |
| 4,957,482 A | 9/1990 | Shiber |

(Continued)

FOREIGN PATENT DOCUMENTS

| | | |
|---|---|---|
| WO | WO 96/01591 | 1/1996 |
| WO | WO 98/38929 | 9/1998 |
| WO | WO 99/44510 | 9/1999 |
| WO | WO 99/44542 | 9/1999 |
| WO | WO 00/41762 | 7/2000 |

OTHER PUBLICATIONS

Schmitz–Rode et al., "New device for percutaneous fragmentation of pulmonary emboli" Radiology (1991) 180:135–137.

Sharafuddin et al. "Current status of percutaneous mechanical thrombectomy. Part I. General Principles" Journal of Vascular and Interventional Radiology (1997) 8(6):911–921.

*Primary Examiner*—Cary E. O'Connor
(74) *Attorney, Agent, or Firm*—Townsend and Townsend and Crew LLP

(57) ABSTRACT

Thrombectomy and other treatments are achieved using a catheter having a positioning cage and a macerator within the positioning cage. The catheter is introduced to a target body lumen, typically a blood vessel, and a positioning cage deployed at a treatment site. The macerator is then operated to disrupt thrombus, clot, or other occlusive materials at the treatment site, and the catheter is used to collect and remove the disruptive materials from the body lumen. In particular examples, the macerator may be radially expansible and optionally rotated and/or axially translated within the positioning cage to effect disruption of the occlusive material.

12 Claims, 14 Drawing Sheets

U.S. PATENT DOCUMENTS

| | | | |
|---|---|---|---|
| 4,979,939 A | 12/1990 | Shiber | |
| 5,002,553 A | 3/1991 | Shiber | |
| 5,007,896 A | 4/1991 | Shiber | |
| 5,024,651 A | 6/1991 | Shiber | |
| 5,030,201 A | 7/1991 | Palestrant | |
| 5,041,082 A | 8/1991 | Shiber | |
| 5,041,093 A | 8/1991 | Chu | |
| 5,100,423 A | 3/1992 | Fearnot | |
| 5,116,352 A | 5/1992 | Schnepp-Pesch et al. | |
| 5,135,531 A | 8/1992 | Shiber | |
| 5,192,268 A | 3/1993 | Shiber | |
| 5,226,909 A | 7/1993 | Evans et al. | |
| 5,306,244 A | 4/1994 | Shiber | |
| 5,330,484 A | 7/1994 | Gunther et al. | |
| 5,334,211 A | 8/1994 | Shiber | |
| 5,419,774 A | 5/1995 | Willard et al. | |
| 5,423,799 A | 6/1995 | Shiu | |
| 5,443,443 A | 8/1995 | Shiber | |
| 5,501,694 A | 3/1996 | Ressemann et al. | |
| 5,540,707 A | 7/1996 | Ressemann et al. | |
| 5,556,408 A | 9/1996 | Farhat | |
| 5,569,275 A | 10/1996 | Kotula et al. | |
| 5,569,277 A | 10/1996 | Evans et al. | |
| 5,571,122 A | 11/1996 | Kelly et al. | |
| 5,597,378 A | 1/1997 | Jervis | |
| 5,616,149 A | 4/1997 | Barath | |
| 5,630,806 A | 5/1997 | Inagaki et al. | |
| 5,643,199 A | 7/1997 | Rowland et al. | |
| 5,653,696 A | 8/1997 | Shiber | |
| 5,681,335 A | 10/1997 | Serra et al. | |
| 5,688,234 A | 11/1997 | Frisbie | |
| 5,695,507 A | 12/1997 | Auth et al. | |
| 5,766,191 A | 6/1998 | Trerotola | |
| 5,795,322 A | 8/1998 | Boudewijn | |
| 5,873,882 A | 2/1999 | Straub et al. | |
| 5,876,414 A | 3/1999 | Straub | |
| 5,904,698 A | 5/1999 | Thomas et al. | |
| 5,911,734 A | 6/1999 | Tsugita et al. | |
| 5,928,186 A | 7/1999 | Homsma et al. | |
| 5,947,985 A | 9/1999 | Imran | |
| 5,954,737 A | 9/1999 | Lee | |
| 5,972,019 A | 10/1999 | Engelson et al. | |
| 6,001,112 A | 12/1999 | Taylor | |
| 6,036,708 A | 3/2000 | Sciver | |
| 6,066,152 A * | 5/2000 | Strauss et al. | 606/170 |
| 6,322,572 B1 | 11/2001 | Lee | |

* cited by examiner

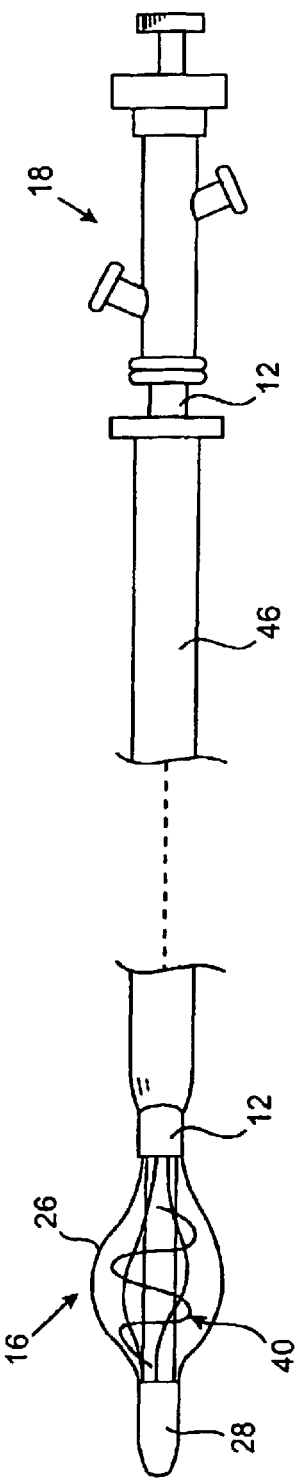
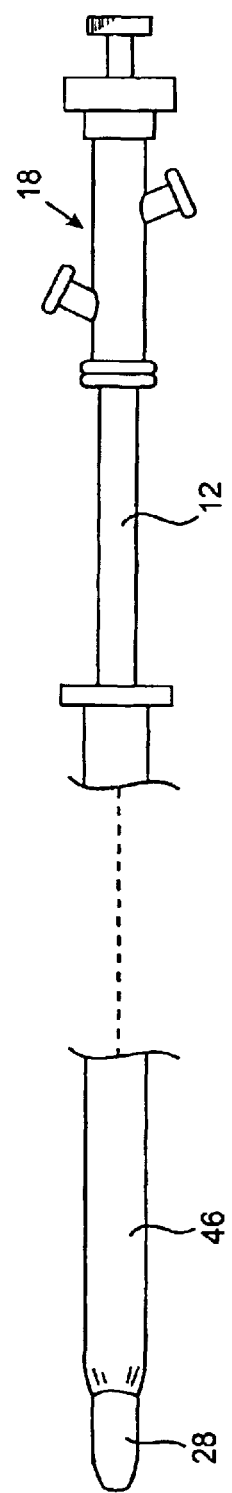
FIG. 3A
FIG. 3B

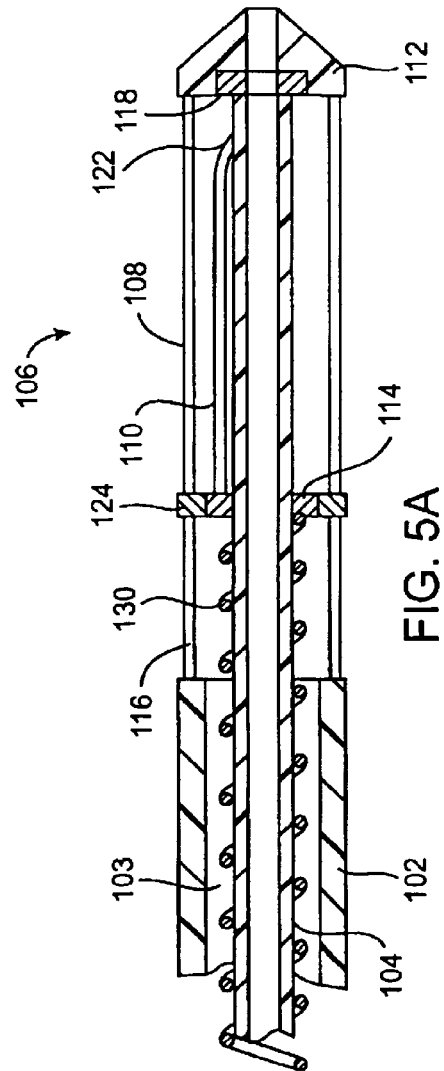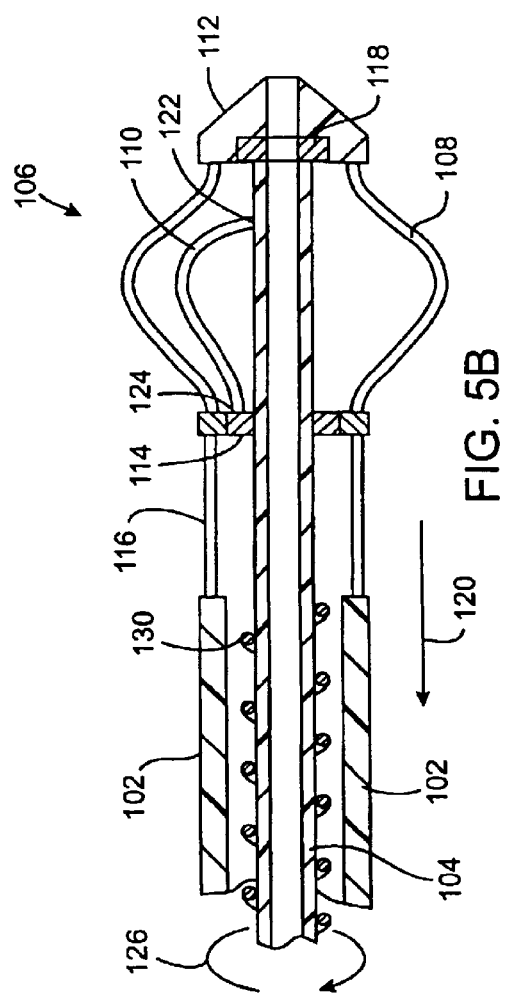

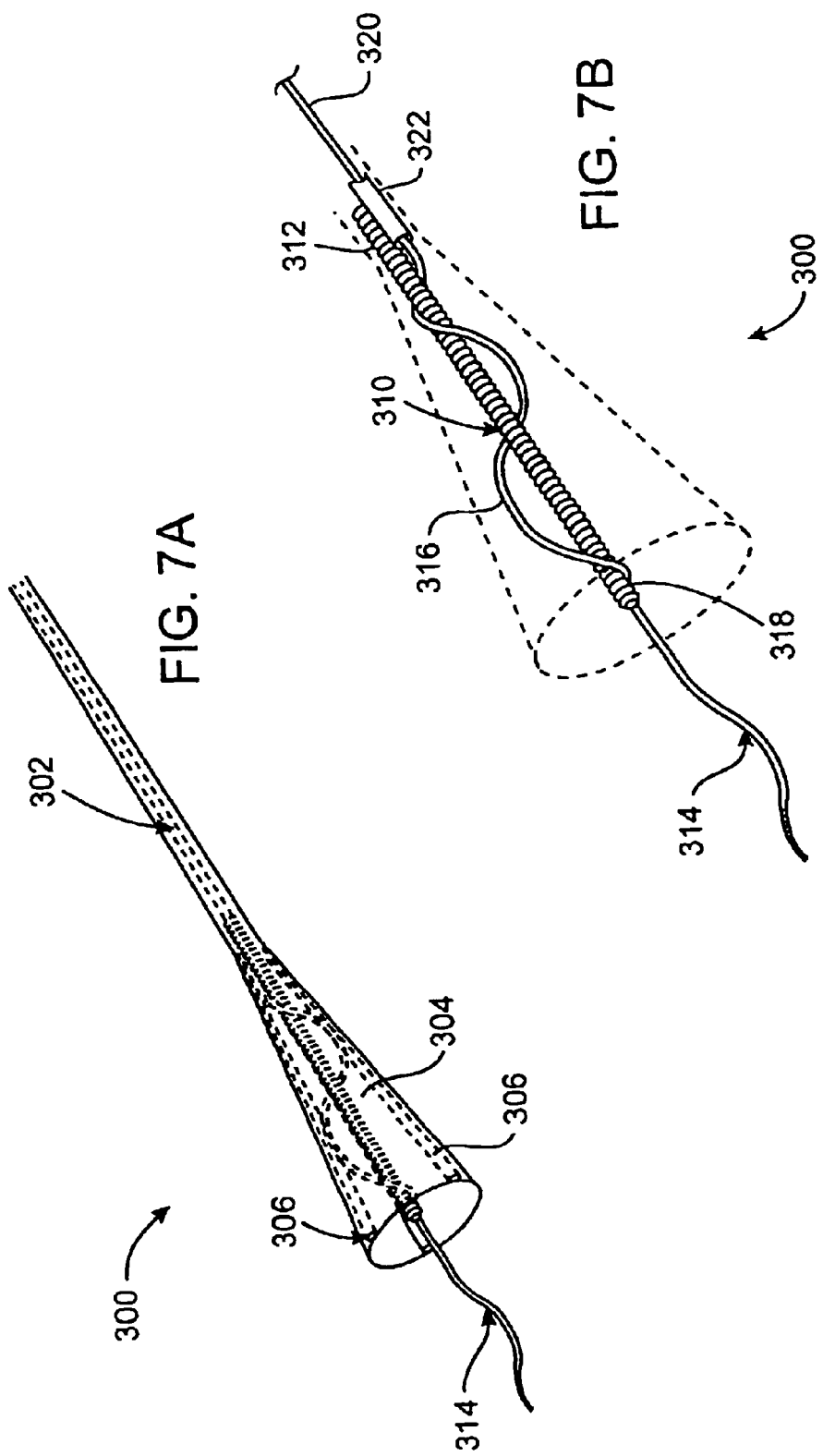

SYSTEMS AND METHODS FOR CLOT DISRUPTION AND RETRIEVAL

CROSS-REFERENCES TO RELATED APPLICATIONS

This present application is a continuation of application Ser. No. 10/162,276, filed Jun. 3, 2002 now U.S. Pat. No. 6,600,014, which was a continuation of application Ser. No. 09/454,517 filed Dec. 6, 1999 now U.S. Pat. No. 6,454,775, the full disclosures of which are incorporated herein by reference.

BACKGROUND OF THE INVENTION

1. Field of the Invention

The present invention relates generally to medical devices and methods. More particularly, the present invention relates to devices and methods for disrupting, collecting, and removing occlusive material from blood vessels and other body lumens.

Thrombosis and atherosclerosis are common ailments which occur in humans and which result from the deposition of thrombus and clot on the walls of blood vessels. When hardened, such deposits are commonly referred to as plaque. Such deposits are most common in the peripheral blood vessels that feed the limbs of the human body and the coronary arteries which feed the heart. Stasis, incompetent valves, and trauma in the venous circulation cause thrombosis, particularly occurring as a deep vein thrombosis in the peripheral vasculature. When such deposits build-up in localized regions of the blood vessel, they can restrict blood flow and cause a serious health risk.

In addition to forming in the natural vasculature, thrombosis is a serious problem in "artificial" blood vessels, particularly in peripheral femoral-popliteal and coronary bypass grafts and dialysis access grafts and fistulas. The creation of such artificial blood vessels requires anastomotic attachment at at least one, and usually at at least two, locations in the vasculature. Such sites of an anastomotic attachment are particularly susceptible to thrombus formation due to narrowing caused by intimal hyperplasia, and thrombus formation at these sites is a frequent cause of failure of the implanted graft or fistula. The arterio-venous grafts and fistulas which are used for dialysis access are significantly compromised by thrombosis at the sites of anastomotic attachment and elsewhere. Thrombosis often occurs to such an extent that the graft needs to be replaced within a few years or, in the worst cases, a few months.

A variety of methods have been developed for treating thrombosis and atherosclerosis in the coronary and peripheral vasculature as well as in implanted grafts and fistulas. Such techniques include surgical procedures, such as coronary artery bypass grafting, and minimally invasive procedures, such as angioplasty, atherectomy, transmyocardial revasculaturization, and the like. Of particular interest of the present invention, a variety of techniques generally described as "thrombectomy" have been developed. Thrombectomy generally refers to procedures for the removal of relatively soft thrombus and clot from the vasculature. Removal is usually achieved by mechanically disrupting the clot, optionally with the introduction of thrombolytic agents. The disrupted thrombus or clot is then withdrawn through a catheter, typically with a vacuum or mechanical transport device.

Thrombectomy generally differs from angioplasty and atherectomy in the type of occlusive material which is being treated and in the desire to avoid damage to the blood vessel wall. The material removed in most thrombectomy procedures is relatively soft, such as the clot formed in deep vein thrombosis, and is usually not hardened plaque of the type treated by angioplasty in the coronary vasculature. Moreover, it is usually an objective of thrombectomy procedures to have minimum or no deleterious interaction with the blood vessel wall. Ideally, the clot will be disrupted and pulled away from the blood vessel wall with no harmful effect on the wall itself.

While successful thrombectomy procedures have been achieved, most have required comprise between complete removal of the thrombosis and minimum injury to the blood vessel wall. While more aggressive thrombectomy procedures employing rotating blades can be very effective at thrombus removal, they present a significant risk of injury to the blood vessel wall. Alternatively, those which rely primarily on vacuum extraction together with minimum disruption of the thrombus, often fail to achieve sufficient thrombus removal.

For these reasons, it would be desirable to provide improved apparatus, systems, methods, and kits for performing thrombectomy procedures. It is particularly desirable that the present invention provide thrombectomy procedures which are both capable of effective thrombus and clot removal while minimizing the risk of injury to the blood vessel wall. The methods and procedures of the present invention should be suitable for treatment of both arteries and veins within the peripheral, coronary, and cerebral vasculature. Even more particularly, the present invention should provide for the treatment of native and synthetic grafts which are subject to thrombosis and clotting, such as arterio-venous grafts and fistulas, bypass grafts, and the like. In addition to treatment of the vasculature, the methods, systems, devices, and kits of the present invention should also be useful for treating other body lumens which are subject to occlusion and blockage due to the presence of occlusive materials within the lumen. At least some of these objectives will be met by the inventions described hereinafter.

2. Description of the Background Art

U.S. Pat. No. 5,904,698, describes a catheter having an expansible mesh with a blade or electrode for shearing obstructive material which penetrates the mesh when the mesh is expanded in a blood vessel. Other catheters having expansible meshes, cages, and/or shearing elements are described in U.S. Pat. Nos. 5,972,019; 5,954,737; 5,795,322; 5,766,191; 5,556,408; 5,501,408; 5,330,484; 5,116,352; and 5,410,093; and WO 96/01591. Catheters with helical blades and/or Archimedes screws for disrupting and/or transporting clot and thrombus are described in U.S. Pat. Nos. 5,947,985; 5,695,501; 5,681,335; 5,569,277; 5,569,275; 5,334,211; and 5,226,909. Catheters having expansible filters at their distal ends are described in U.S. Pat. No. 4,926,858 and PCT publications WO 99/44542 and WO 99/44510. Other catheters of interest for performing thrombectomy and other procedures are described in U.S. Pat. Nos. 5,928,186; 5,695,507; 5,423,799; 5,419,774; 4,762,130; 4,646,736; and 4,621,636. Techniques for performing thrombectomy are described in Sharafudin and Hicks (1997) *JVIR* 8: 911–921 and Schmitz-Rode and G ünthar (1991) *Radiology* 180: 135–137.

BRIEF SUMMARY OF THE INVENTION

The present invention provides apparatus, systems, methods, and kits for removing occlusive material from body lumens. While the present invention is particularly suitable for the removal of thrombus and clot from the vasculature, it will also find use in other body lumens, such as the ureter, urethra, fallopian tubes, bile duct, intestines, and the like. The present invention is advantageous in a number of respects. In particular, the present invention provides for effective removal of the occlusive material from the body lumen. Such removal is effective in both achieving a high degree of removal and minimizing the amount of material which is released into the body lumen. This is a particular advantage in treatment of the vasculature where the release of emboli can be a serious risk to the patient. The present invention achieves such effective removal with minimum risk of injury to the luminal wall. As described in detail below, the present invention employs a macerator for breaking up or "disrupting" the thrombus, clot, or other occlusive material, where the macerator is carefully positioned to minimize or prevent contact with and reduce or eliminate the potential for injury to the luminal wall.

In a first aspect, apparatus according to the present invention comprises a catheter for removing the occlusive material from the body lumen. The catheter comprises a catheter body having a proximal end, a distal end, and a lumen therethrough. A radially expansible positioning cage is disposed on the catheter body near its distal end, and a macerator is disposed within the expansible positioning cage. The macerator is configured to disrupt occlusive material within the cage when the cage is expanded against the luminal wall. The macerator is typically a rotating element, such as a helical or other shaped wire which engages and disrupts the occlusive material. Usually, the disrupted material will also be drawn into the catheter body lumen. Alternatively, the disrupted thrombus can be captured in whole or in part by a second catheter usually introduced downstream from the first catheter with the macerator. The second catheter may also comprise a macerator and, in some instances, the two catheters can be similar or identical. In all cases, the disrupted thrombus may be removed through the catheter lumen by aspiration using an external vacuum source and/or a mechanical pump. As a further alternative, a portion of the expansible cage can be provided with a mesh or other filter membrane to permit blood or other luminal flow past the catheter while entrapping the disrupted clot. When the expansible cage is collapsed, the captured clot will be contained, permitting its withdrawal together with the catheter. Often, the "filtering" cage can be used in combination with an aspiration lumen within the catheter itself and/or a second catheter for capturing the disrupted thrombus. Optionally, thrombolytic agents can also be introduced through the catheter to help disrupt the thrombus and clot, and a vacuum and/or mechanical extraction system can be used to help transport the disrupted clot, thrombus, or other occlusive material through the catheter and out of the patient's body.

The radially expansible positioning cage can take a variety of forms, and will usually be configured to position and maintain the distal end of the catheter body away from the luminal wall, preferably at or near the center region of the body lumen being treated. Usually, the cage will be expansible from an initial width (usually diameter) in the range from 1 mm to 4 mm to an expanded width (diameter) from 2 mm to 40 mm. In some instances, the radially expansible cage will have a resilient but generally uncontrolled diameter, i.e., it will be self-expanding. That is, the cage will simply expand within the body lumen to engage the luminal wall and press against the wall with whatever spring force remains in its structure. In such cases, the cage will usually be initially constrained, e.g., by positioning within an outer tube or sheath, and thereafter released from constraint so that it expands within the body lumen to both anchor and center the catheter therein. Alternatively, and usually preferably, the radially expansible cage will have a selectively adjustable diameter. That is, the size or outer diameter of the cage will be controlled by the user so that the cage can be expanded and deployed against the luminal wall with a desired anchoring force. A variety of specific mechanisms for achieving such controlled expansibility are available, with exemplary systems described below.

The radially expansible positioning cage may have a variety of specific configurations. Most commonly, it will consist of a plurality of wires or filaments arranged in axial, helical, or other circumferentially spaced-apart geometries which provide the desired radial positioning forces while retaining sufficiently large gaps or apertures to permit intrusion of the clot or thrombus. As an alternative to wires, the cage could also employ ribbons, perforated plate structures, and will usually be formed from an elastic material, more usually from a metal having spring memory, such as stainless steel, nitinol, or the like. Alternatively, the cage could be formed from a material which expands and responds to electrical or other stimulus. For example, certain bi-metal structures could be electrically heated to effect expansion. Alternatively, heating at a certain heat memory alloys could also permit selective expansion and contraction of the cage. Other specific designs will also be available.

The macerator may also have a variety of configurations, that will generally be configured to engage and optionally penetrate the occlusive material within the body lumen. Usually, the macerator will have a distal portion which engages the clot and thrombus and which is expansible from an initial width (usually diameter) in the range from 1 mm to 4 mm to an expanded width (diameter) in the range from 2 mm to 35 mm. In the case of thrombus and clot, the macerator will usually be able to penetrate into the mass of thrombus or clot to engage and entangle the fibrin strands therein. By thus "capturing" the thrombus or clot, the macerator can then draw the material away from the luminal wall and break up the material sufficiently so that it may be withdrawn, for example, through the lumen of the catheter, optionally, but not necessarily with mechanical and/or vacuum assistance.

The macerator will usually be radially expansible so that, after the catheter has been centered, the macerator may be deployed and expanded to engage the occlusive material without engaging the luminal wall. While it is possible that the macerator would have a fixed width or diameter (i.e., would be released from constraint to assume its full, unconstrained dimension), the macerator will more usually be capable of being selectively expanded (i.e., the user will be able to selectively expand and collapse the macerator to achieve a desired width or diameter). Most preferably, both the cage and the macerator will be selectively expansible, where the expansion of each can be effected separately from the expansion of the other. That is, in the most preferred embodiments of the present invention, the catheter will have both a positioning cage and a macerator which can each be independently adjusted in their radial width or diameter.

Further preferably, the macerator will be rotatable and/or axially movable to assist in breaking up the occlusive material within the cage and drawing the material into the catheter body. In such cases, the catheter will usually further comprise a drive unit attached or attachable to a proximal end of the catheter body. The drive unit will usually be coupled through a drive cable or shaft to the macerator.

In the most preferred configurations, the macerator will comprise an expansible shaped wire which can be deployed within the positioning cage. The shaped wire may have a generally uniform diameter, but will more usually be non-uniform in diameter, thus being a spiral or other particular geometry. The width of the shaped wire may be adjusted in a variety of ways. For example, two spaced-apart points on the wire may be axially translated relative to each other in order to open or close the helix or other geometry. Alternatively, or additionally, the two spaced-apart points on the shaped wire may be rotated relative to each other in order to achieve expansion and contraction of the wire. Several specific shaped wire macerator designs are presented hereinafter.

In a second aspect, apparatus of the present invention comprises the macerator assemblies. For example, a first embodiment of the macerator comprises a tubular shaft having a proximal end, a distal end, and at least one lumen therethrough. A wire having a distal section and a helical shank is disposed within the tubular shaft so that a distal section of the wire is attached to an exterior location near the distal end of the shaft. The distal section of the wire will be shaped or shapeable so that it can be radially expanded from the tubular shaft to provide a clot disruption structure. In the simplest embodiments, the wire may be expanded to form a simple arc-shaped profile which can be rotated to generate an ovoid path within the clot. Alternatively, the distal section of the wire could have a more complex geometry, such as a helical coil having one, two, three, or more turns on the distal shaft after it is expanded. Other geometries will also be possible. A proximal end of the shank is slidably received in the lumen of the shaft so that the distal section can be radially expanded and contracted by axially translating the shank relative to the shaft. Optionally, the tubular shaft will include only the single lumen which will extend the entire length of the shaft. In that case, the wire will pass into the lumen through a port in the side of the shaft. Preferably, the single internal lumen will have a diameter which is sufficiently large to accommodate both the wire and a separate guidewire, at least over the portions of the shaft where both would be present. In such cases, the internal diameter will usually be at least 0.25 mm, often at least 0.5 mm, preferably at least 1 mm, and sometimes 1.5 mm or larger. Also in such cases, the capture wire will have a diameter in the range from 0.05 mm to 1.5 mm, usually from 0.5 mm to 1.3 mm, at least over that portion of the capture wire which is within the lumen with the guidewire.

In an alternative embodiment, the tubular shaft may include at least two lumens, where the wire is received in a proximal portion of one lumen and the other lumen is configured to receive a guidewire. Usually, the capture wire lumen will terminate proximally of the distal end of the tubular shaft, but the lumen which receives the guidewire will extend the entire length of the shaft.

A second embodiment of the macerator of the present invention comprises a tubular shaft assembly including an outer tube having a proximal end, a distal end, and a lumen therethrough. An inner tube having a proximal end, a distal end, and a lumen therethrough is rotatably and/or slidably received in the lumen of the outer tube, and a wire coil has one end attached to the proximal end of the inner tube and another end attached to the proximal end of the outer tube. Thus, the wire coil can be radially expanded and collapsed by rotating and/or axially translating the inner tube relative to the outer tube.

Both of the macerators just described will find use in combination with any of the catheter systems described earlier in this application.

In another aspect of the present invention, methods for removing occlusive material from a body lumen comprise positioning a macerator so that it is spaced inwardly from (usually centered within) a surrounding wall of the body lumen. The macerator is rotated and/or axially translated to disrupt and optionally capture clot without significant shearing. The disrupted clot may then be withdrawn through a catheter within the body lumen, usually the catheter used to deploy the macerator, or otherwise captured. In the preferred embodiments, the width of the macerator will be adjusted, and the macerator is in the form of a helical wire. In the case of helical wire macerators, width adjustment can be achieved by rotating and/or axially translating spaced-apart points on the wire to achieve a desired helical diameter. Usually, positioning the macerator is achieved by expanding a positioning cage within the body lumen, where the macerator is located within the positioning cage. In such cases, the methods will usually further comprise translating and/or rotating the macerator within the positioning cage.

The present invention still further comprises kits, including a catheter having a macerator near its distal end. The kits will further include instructions for use according to any of the methods set forth above. In addition to the catheter and instructions for use, the kits will usually further comprise packaging, such as a box, pouch, tray, tube, bag, or the like, which holds the catheter and the instructions for use. Usually, the catheter will be maintained sterilely within the package, and the instructions for use will be printed on a separate package insert or piece of paper. Alternatively, the instructions for use may be printed in whole or in part on a portion of the packaging itself.

BRIEF DESCRIPTION OF THE DRAWINGS

FIG. 3A is a side view of a portion of the catheter system of FIG. 1 showing the expansible positioning cage and macerator in their deployed configuration.

FIG. 3B is similar to FIG. 3A, except that the positioning cage and macerator are shown in their non-deployed configuration.

FIG. 5A is a side view of the distal end of the catheter of FIG. 4, shown in section with the positioning cage and macerator in a non-deployed configuration.

FIG. 5B is similar to FIG. 5A, except that the centering cage and macerator are shown in a deployed configuration.

FIGS. 7A and 7B illustrate the distal portion of a fourth embodiment of a clot disruption catheter constructed in accordance with the principles of the present invention.

DETAILED DESCRIPTION OF THE INVENTION

Figure 1:
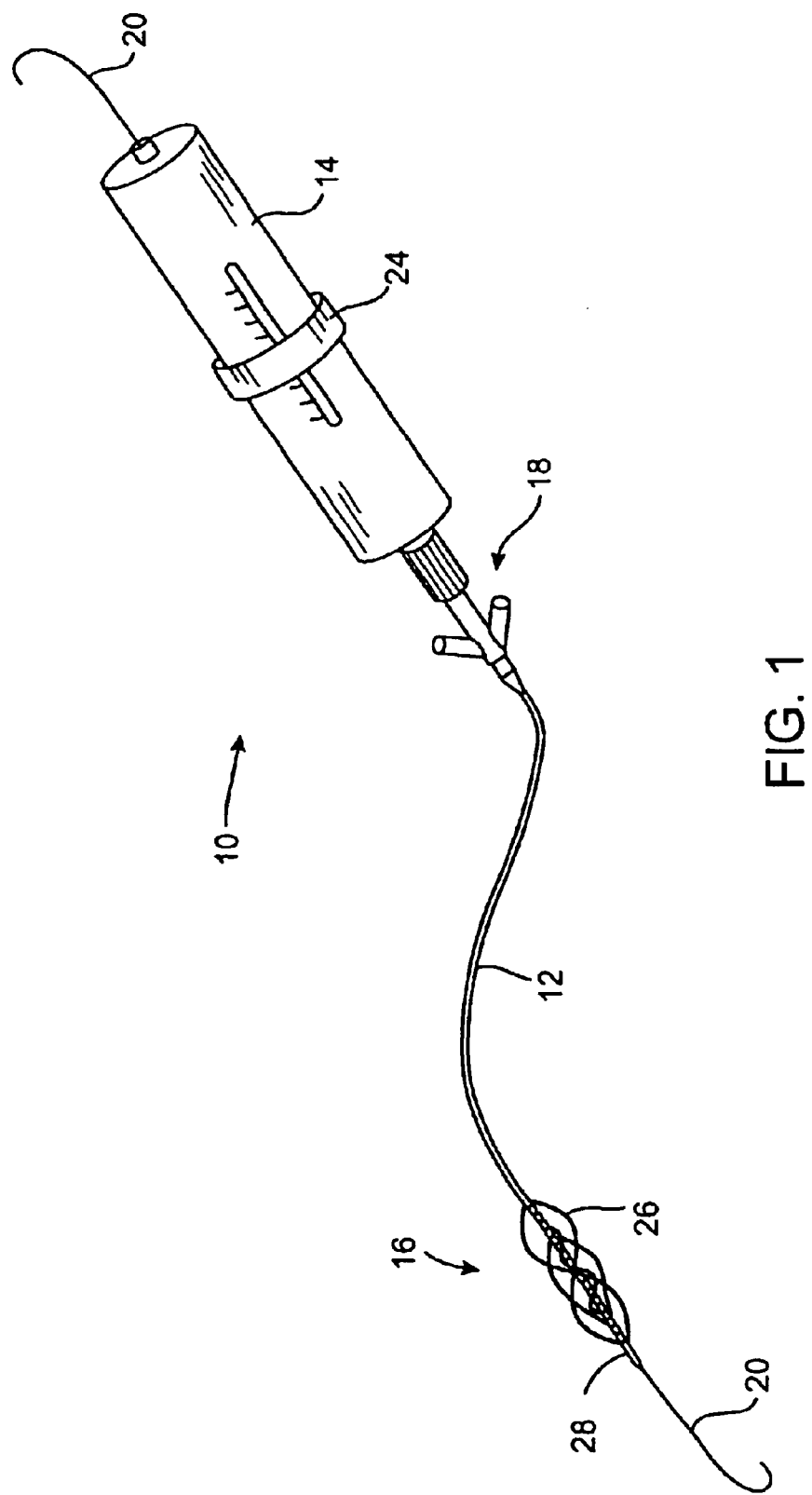
FIG. 1 is a perspective view of a clot disruption catheter system constructed in accordance with the principles of the present invention.

Referring now to FIG. 1, a first embodiment of a clot disruption system 10 constructed in accordance with the principles of the present invention will be described. The clot disruption system 10 includes a clot disruption catheter 12 and a motor drive unit 14. The catheter 12 has a distal section 16 which comprises the expansible cage and macerator components of the catheter, as described in greater detail in connection with FIGS. 2A and 2B. A proximal hub 18 is secured to the proximal end of the catheter 12 and removably connectable to the motor drive unit 14. The motor drive unit 14 will be configured to transmit rotational and/or axial translational forces through a tubular shaft 22 (FIGS. 2A and 2B) to manipulate the macerator. A slidable ring 24 is shown schematically on the motor drive unit 14 and is intended, for example, to permit axial translation of the macerator. Such axial translation, however, is not essential and is only an optional feature of the present invention.

Figure 2A:
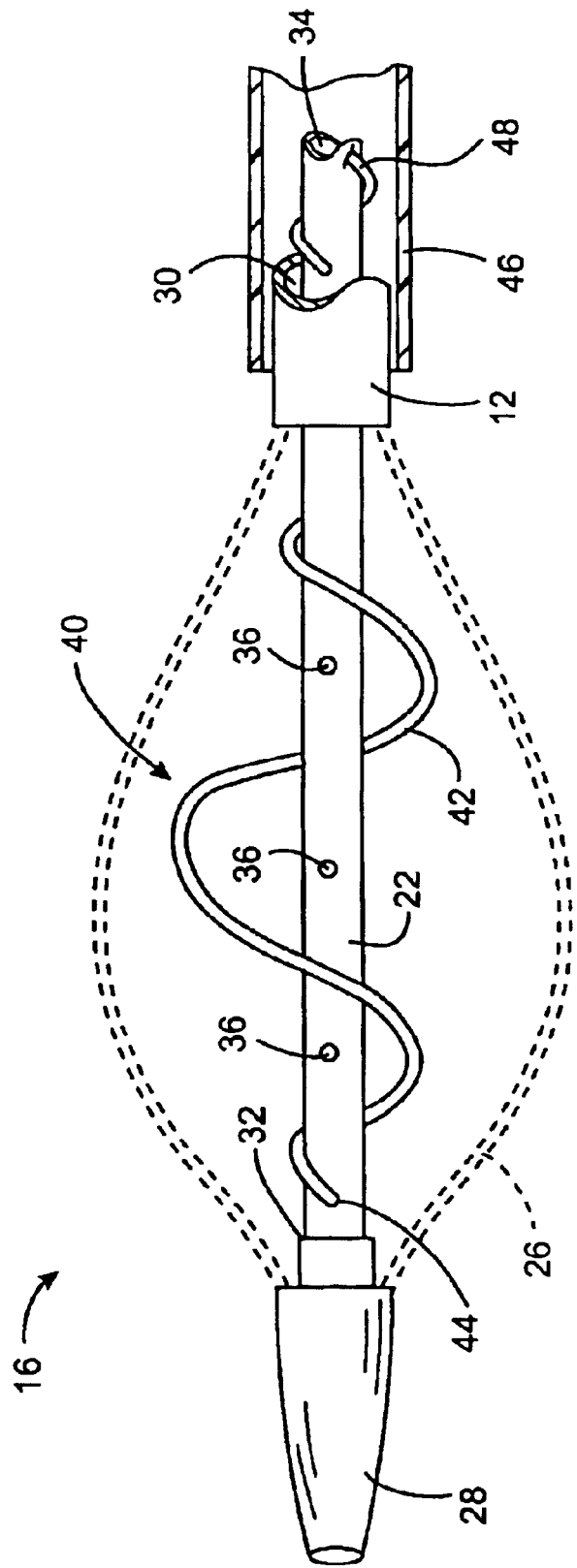
FIG. 2A is a detailed view of the distal end of the clot disruption catheter system of FIG. 1, with portions broken away.

The distal section 16 of the clot disruption catheter 12 is best illustrated in FIG. 2A. The distal section 16 comprises a radially expansible cage 26 which may have any of the forms and structures described above. In particular, cage 26 may comprise a plurality of helical wires or other elements 26A, as illustrated in FIG. 2C. Alternatively, the cage may comprise a plurality of straight, axially aligned wires or other elements 26B, as shown in FIG. 2D. In the catheter 12, the expansible cage 26 will be self-expanding, i.e., it will assume its radially expanded configuration absent any constraining forces. The cage 26 is shown in its expanded configuration in each of FIGS. 1, 2A, 2C, and 2D. The distal tips of the cage elements are attached to a nose cone 28 which may be fixed or floating relative to the main portion of the catheter body 12, as described in more detail below.

The body of clot disruption catheter 12 will have a lumen 30 extending from hub 18 to the distal section 16, and the tubular shaft 22 will be disposed within the lumen 30. A distal end 32 of the tubular shaft 22 will be connected to the nose cone 28, and the shaft will preferably have an inner lumen 34 which terminates in a series of infusion ports 36 (which may be circular, as illustrated or may be elongate slits or may have a variety of other geometries) disposed between the distal end of the body of catheter 12 and the nose cone 28. The lumen 34 and infusion ports 36 will be useful, for example, for delivering thrombolytic and other agents used in connection with clot disruption. The lumen will also receive a guidewire 20 to facilitate positioning within a blood vessel or other body lumen.

Macerator 40 is disposed on the tubular shaft 22 within the expansible cage 26. The macerator 40 is illustrated as a helical wire or filament, but could comprise any of the structures described previously. Helical wire 42 is formed from spring material, typically a spring stainless steel or shape memory alloy, and is fixedly attached to the shaft 22 at both ends. First attachment point 44 is visible in FIG. 2A, while the second attachment point is hidden behind the shaft. With this configuration of wire 42, it will be appreciated that the macerator 40 is self-expanding. Radial compression forces will cause the element 42 to collapse radially inwardly against the exterior of shaft 22.

Macerator 40 comprising helical wire 42 is intended to operate by rotation of the shaft 22. When the shaft 22 is rotating, the helix will trace a generally ovoid shell within the expansible cage 26, thus engaging and disrupting occlusive material which is within the cage. In particular, when treating clot within blood vessels, the helical wire 42 will disrupt the clot and engage and entangle materials within the clot, particularly fibrin fibers which make up a substantial portion of the clot material. By breaking up and engaging the clot in this fashion, the clot is pulled away from the blood vessel wall rather than sheared from the wall as in many prior thrombectomy and atherectomy procedures. In particular, the combination of the expansible positioning cage 26 and the macerator which is spaced radially inward from the shell defined by the cage, clot removal and disruption can be performed with minimum risk of injury to the blood vessel wall.

The expansible cage 26 and macerator 40 will usually be radially collapsed to facilitate introduction and withdrawal of the catheter 12 to and from a target site within the vasculature or other body lumen. The necessary radial constraint can be provided in a number of ways. For example, a tether or filament could be wrapped around both the cage 26 and the macerator 40, with the constraint being removed when the device reaches the target site. Alternatively, the cage 26 and/or the macerator 40 could be composed of a heat memory material, permitting deployment by use of an induced temperature change, e.g., by passing an electrical current through the structures or by infusing a heated or cooled fluid past the structures. Preferably, however, a radial constraint will be provided by a sheath 46 which can be axially advanced to radially collapse both the cage 26 and macerator 40.

Optionally, the catheter 12 may further comprise a mechanical pump to assist in the removal of disrupted clot and other debris which is produced by operation of the macerator. Conveniently, the mechanical pump may comprise a helical rotor 48 which is disposed over the outer surface of the tubular shaft 22, as illustrated in both FIGS. 2A and 2B. Preferably, although not necessarily, the helical rotor 48 will extend from the proximal side of the macerator (helical wire 42) all the way into the interior of the hub 18. In this way, disrupted clot on other fluid materials can be pumped proximally by the rotor 48 (which acts as an "Archimedes screw") as the macerator and tubular shaft are rotated.

Referring now to FIGS. 3A and 3B, the catheter 12 is shown with the distal section 16 in its radially expanded configuration in FIG. 3A. In particular, sheath 46 is proximally withdrawn to permit both the cage 26 and macerator 40 to radially expand to their maximum diameters. Of course, if the catheter 12 were present in a blood vessel or other body lumen, the radial expansion of the cage 26 would be limited by contact with the luminal wall. In order to facilitate introduction or withdrawal of the catheter 12 from the target body lumen, the distal section 16 can be radially collapsed by distally advancing the sheath 46, as shown in FIG. 3B.

Figure 2B:
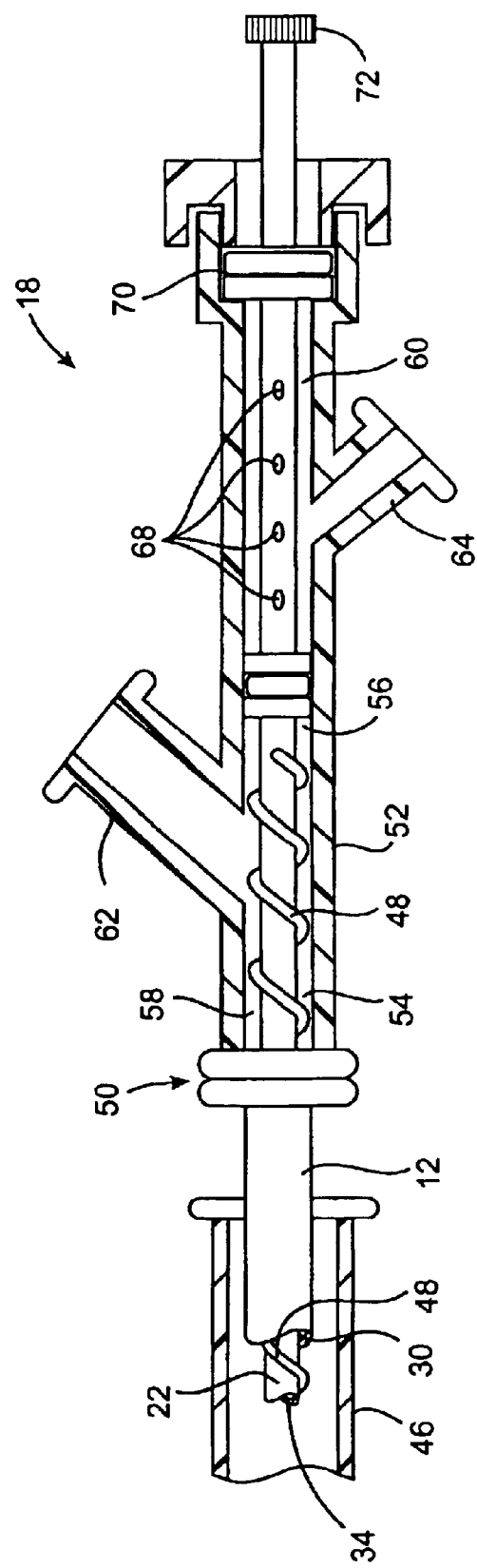
FIG. 2B is a detailed view of a portion of the proximal end of the clot disruption catheter system of FIG. 1, with portions broken away.
Figure 2C:
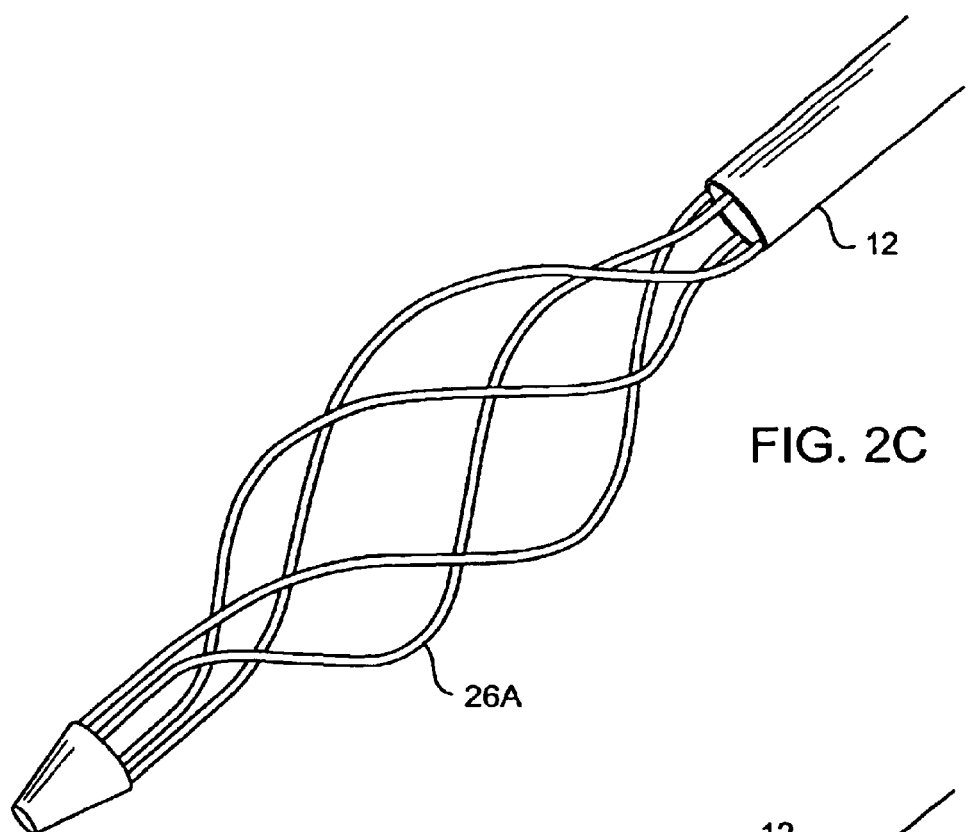
FIG. 2C is a detailed view of a first embodiment of an expansible positioning cage that can be used as part of the clot disruption catheter system of FIG. 1, or any of the other embodiments of the present invention.
Figure 2D:
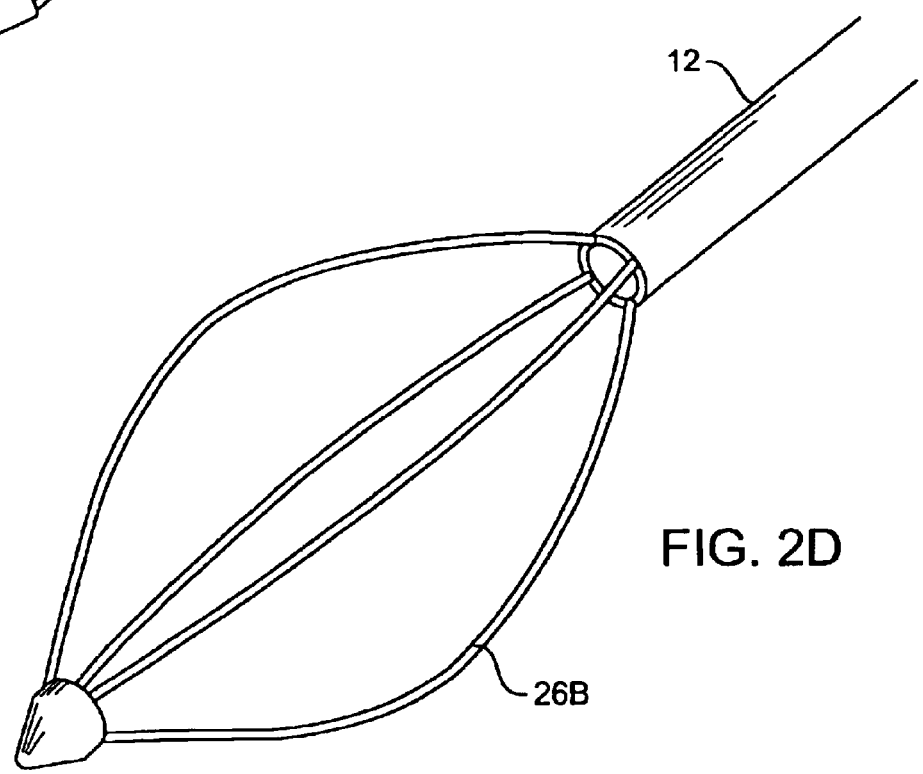
FIG. 2D is a detailed view of an alternative expansible positioning cage that can be used with any of the embodiments of the present invention.

Referring now to FIG. 2B, the construction of proximal hub 18 will be described. A rotating hemostatic fitting 50 is provided at the proximal end of catheter 12 and mates with the distal end of hub body 52. Tubular shaft 22 passes from the lumen 30 of catheter 12 into the interior 54 of hub body 52. A rotating hemostatic seal structure 56 is also provided within the interior 54 and divides the interior into a first isolated region 58 and a second isolated region 60. The first isolated region 58 has connector branch 62 which permits aspiration of fluids and materials through the lumen 30 of catheter 12. A second connector branch 64 opens to the second isolated region 60 and permits infusion of therapeutic agents, such as thrombolytic agents, into the lumen 34 of the tubular shaft 22 through ports 68. A rotating seal 70 is provided at the proximal end of the hub and a hemostatic valve 72 is provided on the proximal end of tubular shaft 22 to permit introduction of a guidewire. The connector 72 will also be suitable for coupling to the motor drive unit 14 to permit rotation of shaft 22 which in turn rotates the macerator 40. Note that the hub 18 illustrated in FIG. 2B is not suitable for axial translation of the shaft 22 relative to the catheter 12.

Figure 4:
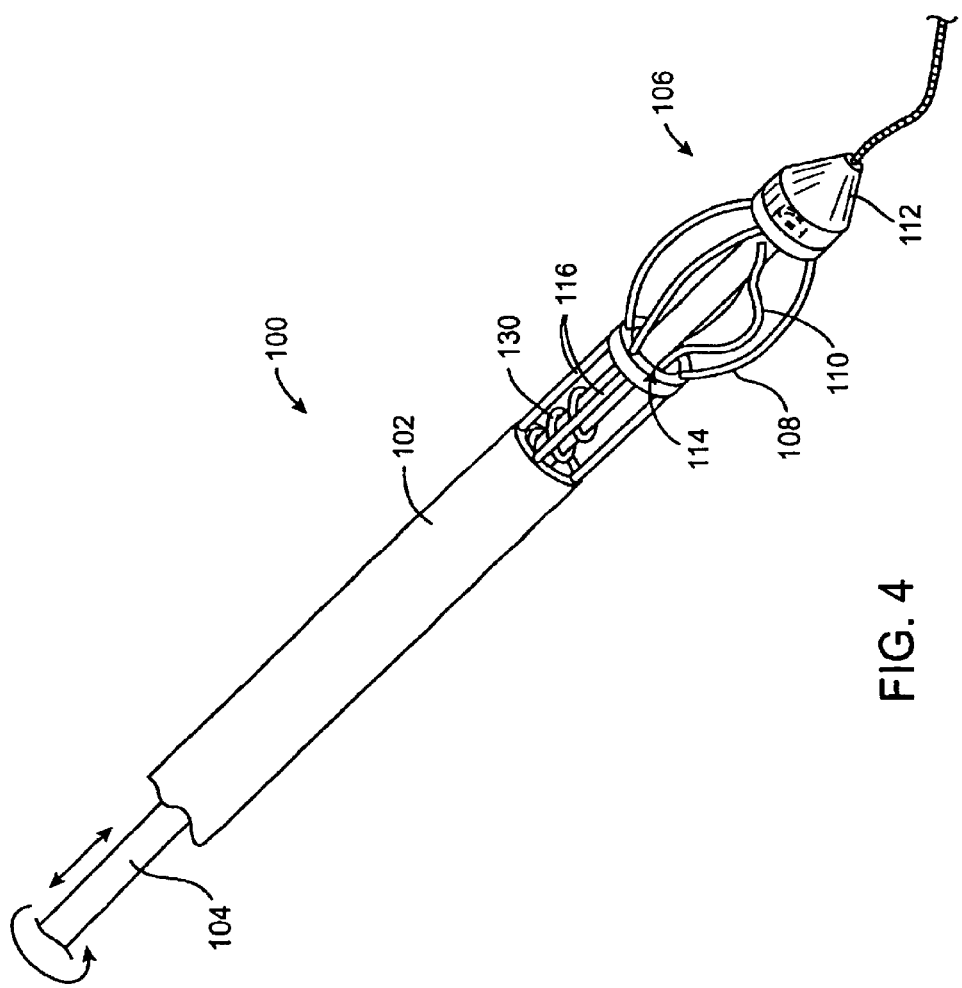
FIG. 4 is a perspective view of a distal portion of a second embodiment of a clot disruption catheter constructed in accordance with the principles of the present invention.

Referring now to FIGS. 4, 5A and 5B, a second exemplary clot disruption catheter 100 will be described. The catheter 100 includes a catheter body 102 and a tubular shaft 104 which is rotatably and axially slidably received in a lumen of the catheter body. The catheter 100 has a distal section 106 including a radially expansible cage 108 and a macerator 110 in the form of an arcuate wire. In contrast to catheter 12 of the first embodiment, both the expansible cage 108 and macerator 110 will be selectively and controllably expansible in the clot disruption catheter 100.

Referring in particular to FIGS. 5A and 5B, the tubular shaft 104 extends through lumen 103 of the catheter body 102 and terminates in a nose cone 112. A bearing structure 114 receives the tubular shaft 104 and permits both rotation and axial translation thereof relative to the catheter body 102. While the bearing 114 could be positioned directly on the distal tip of the catheter body 102, that would block lumen 103 and prevent collection of disrupted clot or other occlusive material therein. Thus, it is desirable to mount the bearing structure 114 distal to the distal end of catheter body 102, e.g., on spacer rods 116, to provide an opening or gap which permits aspiration of disrupted clot or other material through the lumen 103. The distal end of tubular shaft 104 is mounted in a second bearing structure 118 located in the nose cone 12. Bearing structure 118 permits rotation but not axial translation of the shaft 104. Thus, when the shaft 104 is drawn proximally in the direction of arrow 120 (FIG. 5B), the distance between the nose cone 12 and the bearing structure 114 is reduced. This causes the elements of cage 108 to axially shorten and radially expand. While the elements of cage 108 are shown as axial wires or filaments, it will be appreciated that they could be helical or have any one of a variety of other configuration which would permit radial expansion upon axial contraction. Similarly, the macerator wire 110 is fixedly attached to the tubular shaft 104 at an attachment point 122. The other end of the macerator wire 110 is connected at attachment point 124 to the portion of bearing structure 114 which rotates together with the tubular shaft 104. In this way, the macerator is both axially shortened so that it radially expands and is able to rotate when the tubular shaft 104 is rotated, e.g., in the direction of arrow 126.

Optionally, the clot disruption catheter 100, or any of the other clot disruption catheters described herein, may include a mechanical pump component to assist in extraction of clot or other disrupted materials through the lumen of the catheter. As best seen in FIGS. 5A and 5B, the mechanical pump may comprise a simple helical screw, such as a helically wound wire or other element 130. Such a helical screw pump is commonly referred to as an "Archimedes" screw pump and operates by creating a vortical flow as the screw pump is rotated. While in some instances use of the screw pump may be sufficient in itself to remove materials, the screw pump will most often be used in combination with vacuum aspiration to remove materials through the lumen of the catheters.

Figure 6A:
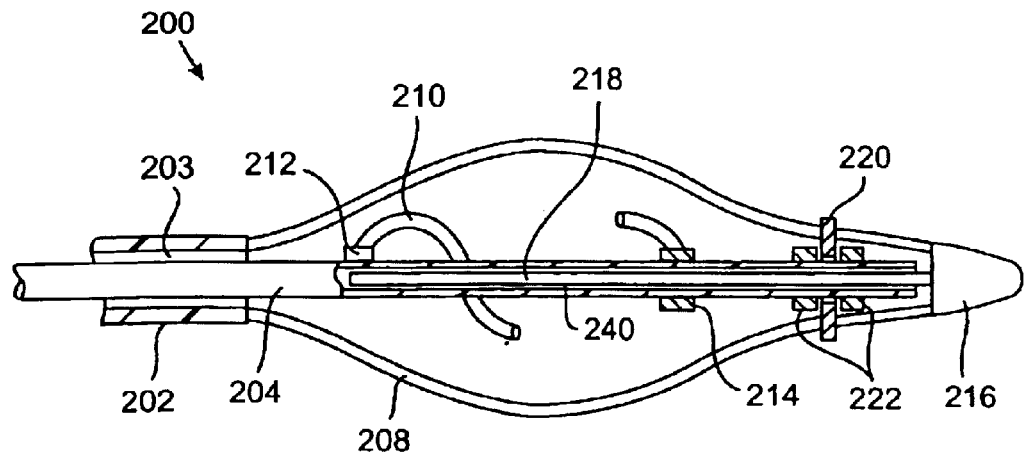
FIGS. 6A and 6B illustrate a distal portion of a third embodiment of the clot disruption catheter of the present invention shown in the deployed and non-deployed configurations, respectively.
Figure 6B:
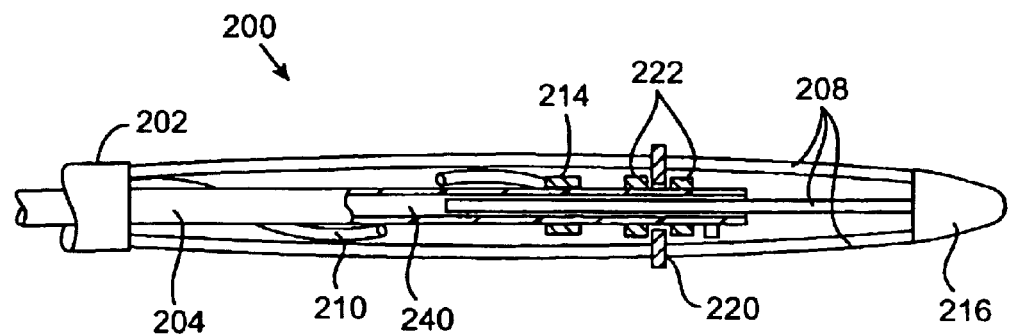

Thus far, clot disruption catheter embodiments have been shown where both the expansible positioning cage and the macerator are self-expanding and where expansion of the cage and macerator are mechanically coupled together, i.e., neither the cage nor the macerator may be expanded or contracted independent of the other. The present invention contemplates other embodiments where either or both of the expansible cage and the macerator may be independently expanded and where the other may optionally be self-expanding. For example, as shown in FIGS. 6A and 6B, a clot disruption catheter 200 comprises a catheter body 202 having a tubular shaft 204 and a lumen 203 thereof. The shaft 204 has a macerator 210 in the form of a helical wire which is fixedly attached at point 212 and slidably attached at point 214. In contrast with the previous embodiments, the tubular shaft 204 is not connected to nose cone 216, but instead floats on a rod 218 which extends proximally from the nose cone. A contraction sleeve 220 is slidably received over the wires which form cage 208 in such a way that proximal movement of the sleeve 220 (relative to the position shown in FIG. 6A) will cause the cage to radially collapse, i.e., as shown in FIG. 6B. Proximal translation of the sleeve 220 can be effected by proximally drawing tubular shaft 204 so that constraining bearings 222 on the shaft draw the sleeve 220 in the proximal direction together with the shaft. Thus, selective expansion and contraction of the cage 208 can be effected by axial movement of the tubular shaft 204 relative to the catheter body 202. Structural integrity of the catheter will be maintained by presence of the rod 218 within the distal end of the lumen 240 within the tubular shaft 204.

Proximal motion of the sleeve 220, however, does not directly collapse the macerator 210. Instead, the macerator 210 is collapsed by a combination of forces. First, the proximal attachment point 212 is drawn into lumen 203 of the catheter body 202, thus constraining the macerator and causing its partial collapse. The remainder of the macerator will be collapsed by the force of the cage structure 208 as it is drawn inwardly by the sleeve 220. The floating attachment point 214 will move over the outer surface of the tubular shaft 204 to accommodate the radial collapse. Thus, the embodiment of FIGS. 6A and 6B illustrates the selective radial expansion and contraction of the positioning cage 208 and the self-expansion of the macerator 210 in response to expansion and contraction of the cage.

A fourth exemplary clot disruption catheter 300 is illustrated in FIGS. 7A and 7B. The clot disruption catheter 300 comprises catheter body 302 having an expansible cage 304 at its distal end. In contrast to previous embodiments, the expansible cage 304 is in the form of a conical "funnel" which may be formed from impervious materials (which will not permit the bypass of blood or other luminal flows) or from "filtering" materials which will permit blood or other bypass flows. Preferably, the funnel will be formed from pervious materials, such as wire meshes, perforate membranes, woven fabrics, non-woven fabrics, fibers, braids, and may be composed of polymers, metals, ceramics, or composites thereof. The filters will have a pore size selected to permit blood flow (including blood proteins) but capture disrupted clot and other embolic debris. Useful pore sizes will be in the range from 20 μm to 3 mm.

The funnel will usually be formed from a flexible filter material and supported on a plurality of rods 306 which can be actively or passively deflected in order to open or close the conical cage. Most simply, the rod members 206 will be resilient and have a shape memory which opens the cage structure in the absence of radial constraint. Thus, catheter 300 may be conveniently delivered through a sheath, in a manner analogous to that described in connection with FIG. 1. The clot disruption catheter 310 further includes a macerator assembly 310, best observed in FIG. 7B. The macerator comprises a tubular shaft 312, such as a highly flexible coil shaft adapted to transmit rotational torque. Tubular shaft 312 will include an internal lumen to permit introduction over a guidewire 314. A helical macerator wire 316 has a distal end 318 attached to the distal end of shaft 312. A proximal portion 320 of the macerator 316 extends through a tube 322 attached to the side of the tubular member 312. In this way, the helical portion of macerator 316, which has a helical memory shape, can be expanded and contracted by axially translating the proximal portion 320. Although illustrated passing through a separate tubular member 22, the proximal portion 320 could pass through the same lumen of the tubular shaft 316 as does the guidewire 314. It will be appreciated that the macerator structure 316 could be employed with any of the previous embodiments where it is desired to provide for selective expansion and contraction of the macerator.

Figure 8A:
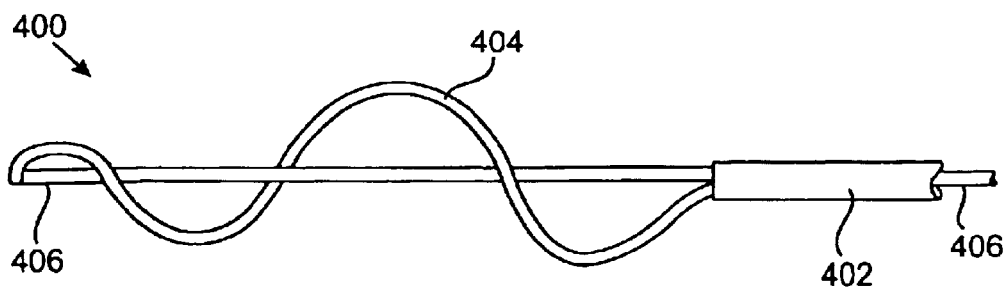
FIGS. 8A–8C illustrate a macerator having a helical wire and methods for its deployment.
Figure 8B:
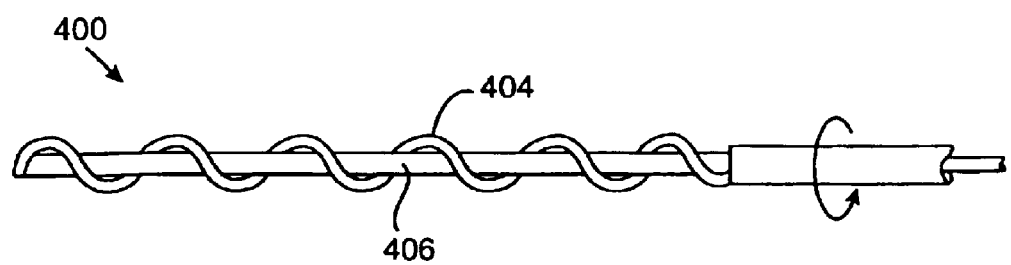
Figure 8C:
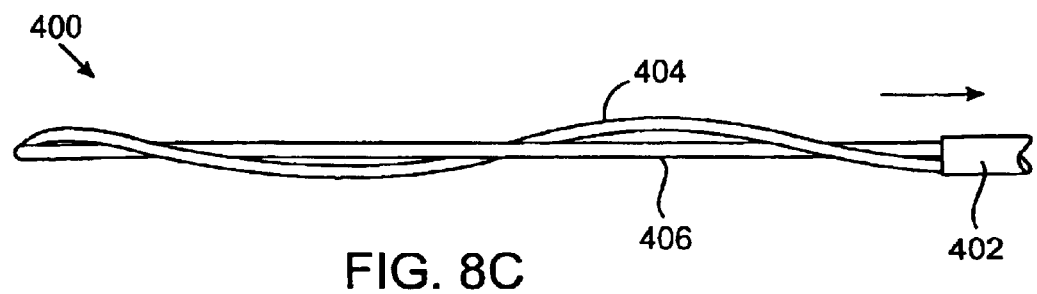

An alternative embodiment of a macerator 400 mounted at the distal end of the tubular shaft 402 is illustrated in FIGS. 8A–8C. A macerator 400 comprises a helical wire 404 having a distal end secured to the distal tip of a rod 406. The rod 406 is slidably and/or rotatably positioned within a lumen of the tubular shaft 402. Thus, by rotating the tubular shaft 402 relative to the rod 406, as shown in FIG. 8B, the helical portion of macerator 404 can be wound down (or wound away from) the rod 406. Alternatively, by axially translating the tubular body 402 relative to the rod 406, the macerator 404 can also be collapsed, as shown in FIG. 8C. It will be appreciated that these macerator embodiments can be utilized in any of the previously described embodiments of the clot disruption catheters of the present invention.

Figure 9:
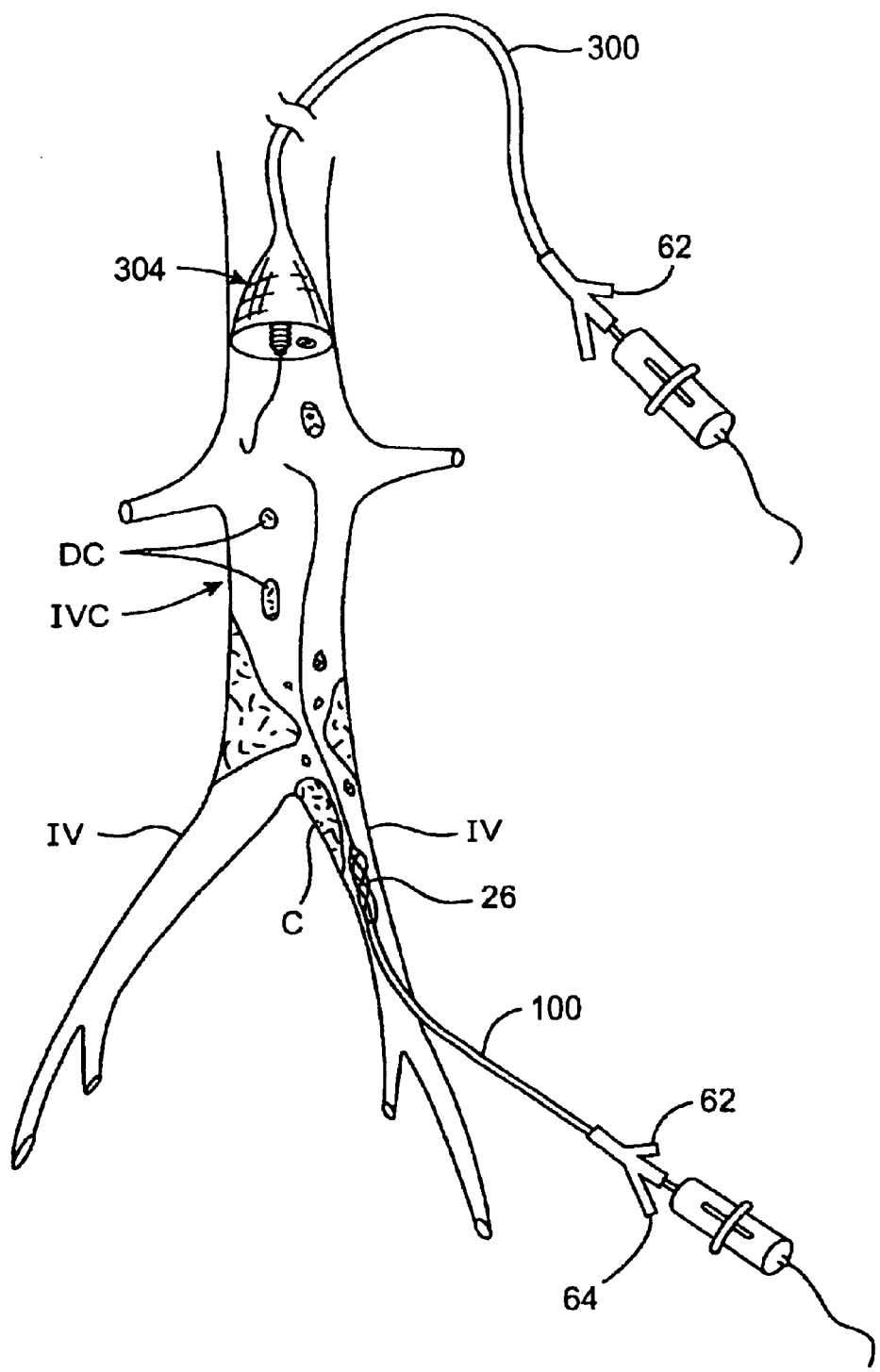
FIG. 9 illustrates a method according to the present invention employing the catheters of FIG. 1 and FIGS. 7A and 7B in combination.

Referring now to FIG. 9, use of clot disruption catheter 100 and clot disruption catheter 300 for performing a procedure in accordance with the principles of the present invention will be described. The catheters 100 and 300 are introduced to a region within the patient's venous system, e.g., at the junction between the iliac veins IV and the inferior vena cava IVC. Blood flow is in the direction from bottom to top, and catheter 100 is introduced into the iliac vein IV in an antegrade direction, i.e., in the direction of blood flow. Catheter 300 is introduced into the inferior vena cava IVC in a retrograde direction, i.e., against the flow of blood. Filtering cage 304 is expanded so that the distal end of the "funnel" engages and generally seals around the interior wall of the inferior vena cava. Positioning cage 26 on catheter 100 is advanced into a region of clot C within the iliac vein IV and the macerator (not shown) is activated in order to disrupt the clot. Optionally, aspiration (and/or mechanical pumping) will be applied through port 62 in order to draw a portion of the disrupted clot out of the patient's vasculature. Further optionally, a thrombolytic agent may be introduced through port 64. Pieces of the disrupted clot DC, however, may be released into the blood flow so that they pass from the iliac vein IV into the inferior vena cava. By positioning the funnel-like cage 304 of catheter 300 within the inferior vena cava, however, the disrupted clot may be captured and, optionally, further disrupted using the macerator assembly within catheter 300. This material may then be aspirated through port 62, optionally being transported using a mechanical pump as elsewhere described herein.

Figure 10A:
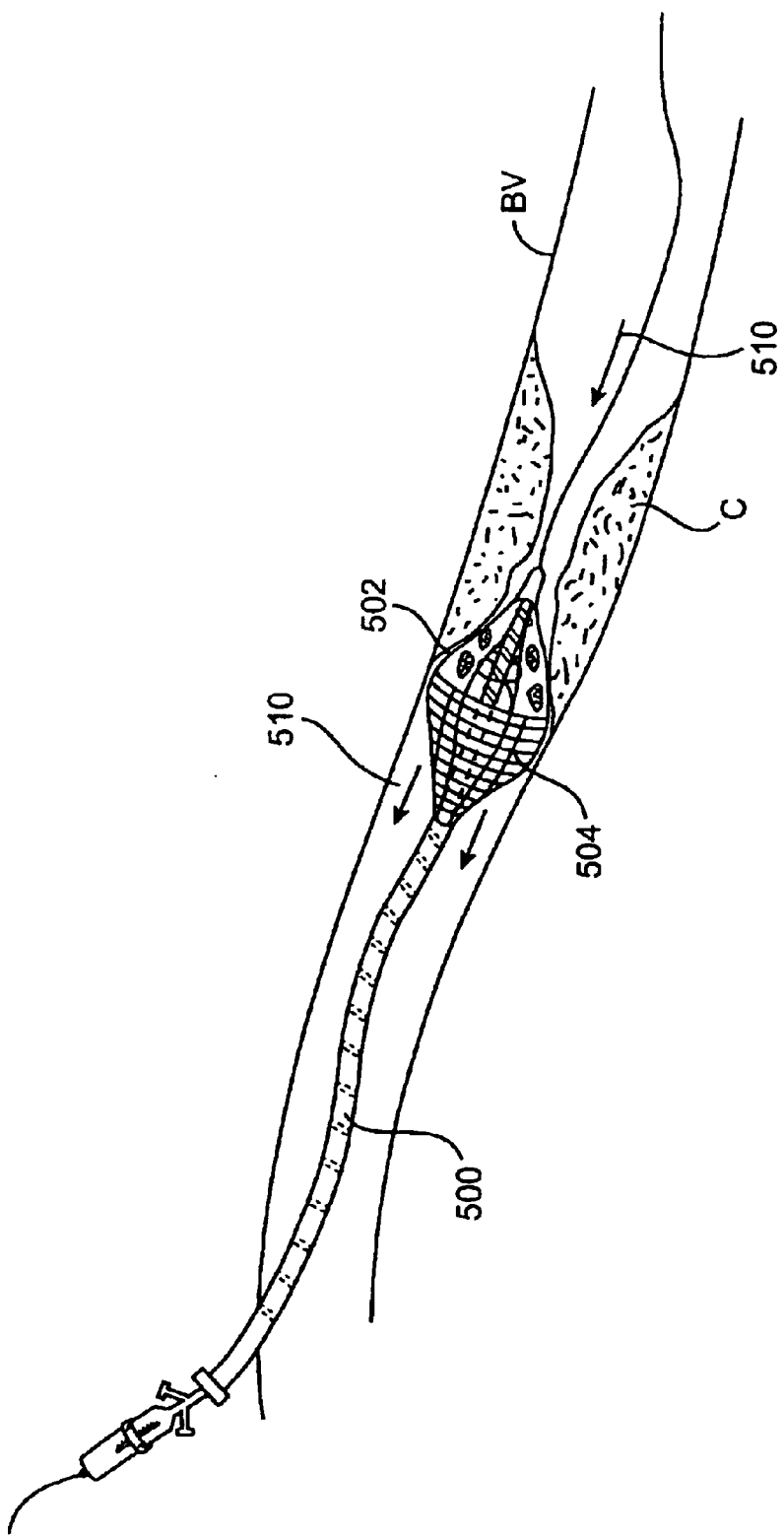
FIGS. 10A and 10B illustrate a modified clot disruption catheter having a filtering structure over a portion of the expansible cage and methods for its use.
Figure 10B:
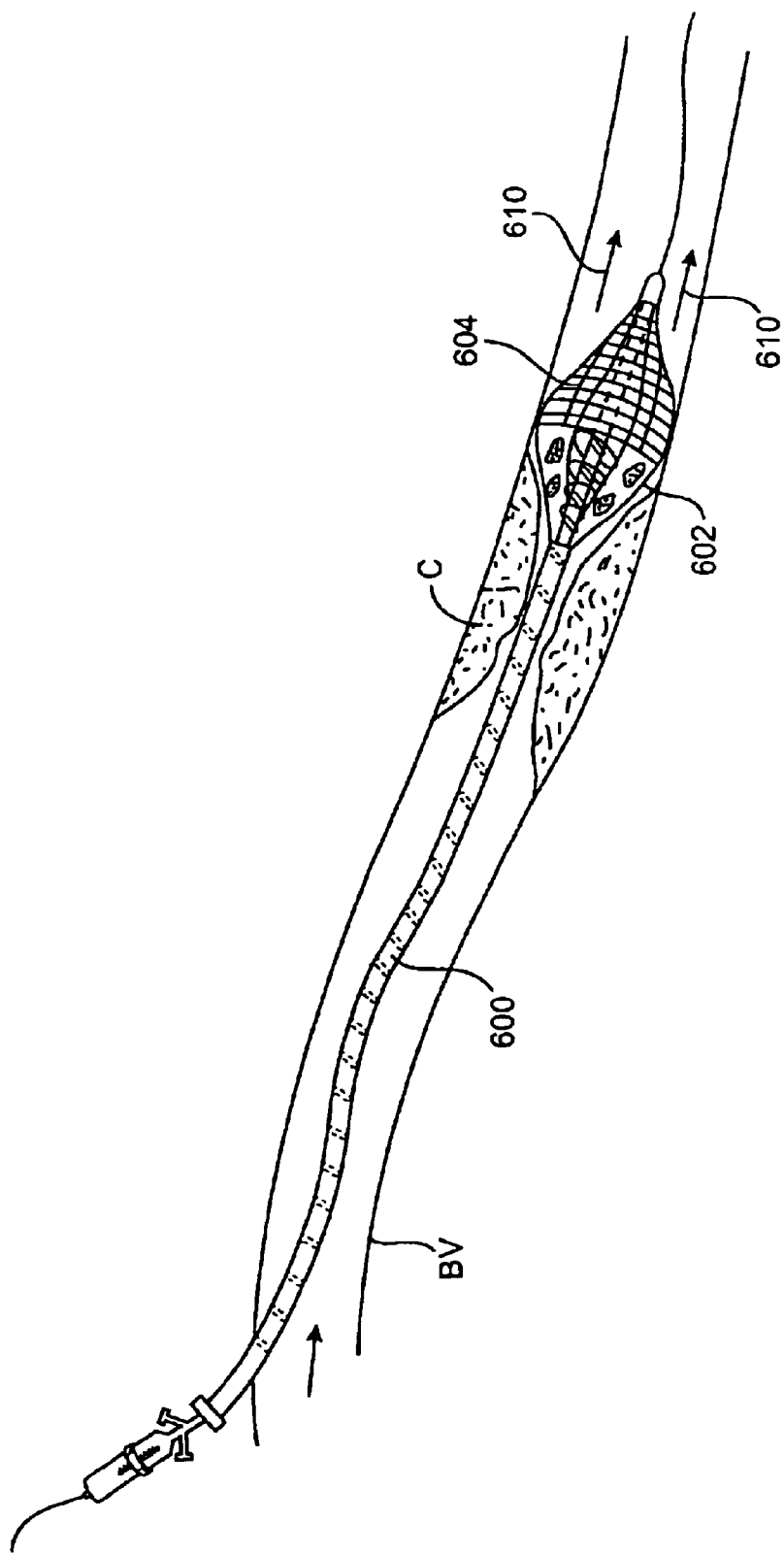

As just described, blood or other luminal filtering can be used advantageously in connection with the devices and methods of the present invention. While a funnel-like cage was described as part of catheter 300, the other cage structures described herein can also be provided with a filtering membrane, mesh, or other porous structure as illustrated in FIGS. 10A and 10B. In FIG. 10A, a clot disruption catheter 500, which may have any of the specific structures described previously (except for that of catheter 300), has an expansible positioning cage 502 at its distal end. A filtering membrane or mesh 504 is formed over the proximal half of the cage 502. The catheter 500 will be particularly useful for treating clot C in a blood vessel B in a retrograde direction, i.e., where the catheter is introduced in a direction against that of blood flow, as shown by arrows 510. The disrupted clot material captured within the filter 504 may be aspirated through the catheter and/or captured within the mesh as the mesh is collapsed.

Catheter 600 (FIG. 10B) is similar to catheter 500 and includes an expansible cage 602 having a membrane or mesh filter element 604 thereon. The filter element 604 is disposed over the distal half or portion of the expansible cage 602, rather than the proximal half. Thus, the catheter 600 is particularly useful for treating clot or thrombus using an antegrade approach, i.e., where the catheter is introduced in the direction of blood flow as shown by arrows 610. In particular, the catheter 600 may be introduced to a blood vessel BV in a conventional manner and pass through a region of clot C so that the expansible cage 604 lies beyond the clot. The catheter may then be drawn proximally so that the internal macerator can disrupt the clot. The disrupted clot will then be collected within the filter 604, and can withdrawn from the blood vessel by collapsing the filter together with the cage.

Figure 11:
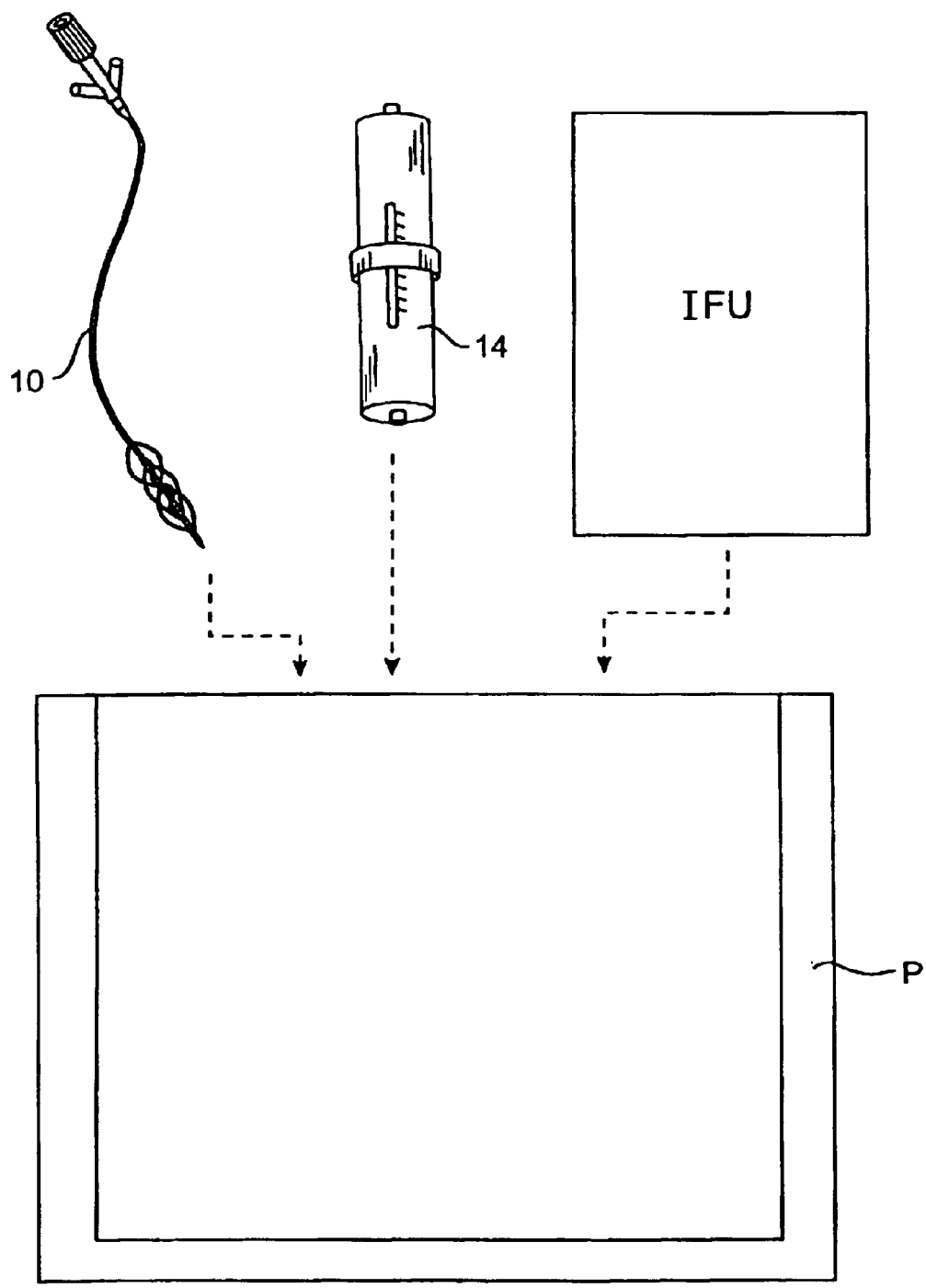
FIG. 11 illustrates a kit constructed in accordance with the principles of the present invention.

Turning now to FIG. 11, the present invention further comprises kits which include at least a catheter, which is shown to be catheter 100 but can be any other catheter capable of disrupting clot in accordance with the methods of the present invention. The kit will further include instructions for use IFU setting forth any of the methods described above. Optionally, the kit may further comprise a motor drive unit 14 or other kit components, such as a guidewire, a thrombolytic agent, or the like. Usually, the kit components will be packaged together in a pouch P or other conventional medical device packaging, such as a box, tray, tube, or the like. Usually, at least the catheter component will be sterilized and maintained sterilely within the package. Optionally, the motor drive unit may not be included with the kits, but may instead be provided as a reusable system component. In that case, usually, the catheter will be disposable.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for thrombus in a blood vessel, said method comprising:
   positioning a catheter within a region of thrombus in the blood vessel;
   centering the catheter along an axis of the blood vessel within a positioning cage;
   releasing a thrombolytic agent through the catheter to said region;
   rotating a macerator to disrupt the clot; and
   aspirating disrupted clot through a lumen in the catheter body while rotating a helical rotor in said lumen to assist in aspiration.

2. A method as in claim 1, wherein releasing comprises infusing the thrombolytic agent from a port within the positioning cage.

3. A method as in claim 2, wherein releasing comprises infusing the thrombolytic agent from a plurality of axially spaced-apart ports within the positioning cage.

4. A catheter for removing occlusive material from a body lumen, said catheter comprising:
   a catheter body having a proximal end, a distal end, and a lumen therethrough;
   a radially expansible positioning cage near the distal end of the catheter body;
   a radially expansible macerator configured to break up occlusive material within the cage and draw the material into the catheter body lumen; and
   a helical rotor within the lumen of the catheter body; and
   a connection on the proximal end of the lumen for aspirating material disrupted by the macerator from within the cage.

5. A catheter as in claim 4, further comprising means for selectively adjusting the diameter of the radially expansible positioning cage.

6. A catheter as in claim 4, wherein the radially expansible cage is self-expanding and has a predetermined unconstrained diameter.

7. A catheter as in claim 4, further comprising means for selectively adjusting the diameter of the macerator.

8. A catheter as in claim 4, wherein the macerator is self-expanding and has a predetermined unconstrained diameter.

9. A catheter as in claim 4, wherein the cage is expansible from an initial width in the range from 1 mm to 4 mm to an expanded width in the range from 2 mm to 40 mm and the macerator has an initial width in the range from 1 mm to 4 mm and an expanded width in the range from 2 mm to 35 mm.

10. A catheter as in claim 4, wherein adjustment of the radial dimension of the macerator is not coupled to expansion of the positioning cage.

11. A catheter as in claim 4, wherein the macerator is rotatable.

12. A catheter as in claim 11, further comprising a drive unit at the proximal end of the catheter body, wherein the drive unit is mechanically coupled to the macerator.

* * * * *

UNITED STATES PATENT AND TRADEMARK OFFICE
CERTIFICATE OF CORRECTION

PATENT NO. : 6,945,977 B2 Page 1 of 1
APPLICATION NO. : 10/680367
DATED : September 20, 2005
INVENTOR(S) : Denise Demarais et al.

It is certified that error appears in the above-identified patent and that said Letters Patent is hereby corrected as shown below:

At Column 1, line 8, please change "6,600,014" to read corrected as --6,660,014--.

Signed and Sealed this

Twenty-ninth Day of July, 2008

JON W. DUDAS
*Director of the United States Patent and Trademark Office*